(12) United States Patent
Osvath

(10) Patent No.: US 9,186,083 B2
(45) Date of Patent: Nov. 17, 2015

(54) METHOD AND SYSTEM FOR SLEEP STAGE DETERMINATION

(75) Inventor: Laszlo Osvath, Brampton (CA)

(73) Assignee: Natus Medical Incorporated, San Carlos, CA (US)

( * ) Notice: Subject to any disclaimer, the term of this patent is extended or adjusted under 35 U.S.C. 154(b) by 1209 days.

(21) Appl. No.: 12/708,637

(22) Filed: Feb. 19, 2010

(65) Prior Publication Data

US 2010/0217146 A1    Aug. 26, 2010

Related U.S. Application Data

(60) Provisional application No. 61/154,796, filed on Feb. 24, 2009.

(51) Int. Cl.
*A61B 5/04* (2006.01)
*A61B 5/0478* (2006.01)
*A61B 5/00* (2006.01)

(52) U.S. Cl.
CPC ............. *A61B 5/0478* (2013.01); *A61B 5/4812* (2013.01); *A61B 5/7264* (2013.01)

(58) Field of Classification Search
CPC .. A61B 5/0476; A61B 5/048; A61B 5/04012; A61B 5/4821; A61B 5/0042; A61B 5/0488; A61B 5/6868; A61B 5/04004; A61B 5/4064; A61B 5/4806; A61B 5/0448; A61M 2230/10
USPC .................................................. 600/544, 545
See application file for complete search history.

(56) References Cited

U.S. PATENT DOCUMENTS

| 5,154,180 | A | 10/1992 | Blanchet et al. |
| 5,299,118 | A | 3/1994 | Martens et al. |
| 5,813,993 | A | 9/1998 | Kaplan et al. |
| 5,999,846 | A | 12/1999 | Pardey et al. |
| 6,272,378 | B1 | 8/2001 | Baumgart-Schmitt |
| 7,299,088 | B1 | 11/2007 | Thakor et al. |
| 7,894,890 | B2 * | 2/2011 | Sun et al. ...................... 600/544 |
| 2007/0179399 | A1 * | 8/2007 | Viertio-Oja et al. .......... 600/559 |
| 2007/0270706 | A1 * | 11/2007 | Merilainen et al. ........... 600/544 |
| 2008/0009753 | A1 * | 1/2008 | Lapinlampi et al. .......... 600/483 |
| 2008/0154111 | A1 | 6/2008 | Wu et al. |
| 2009/0024044 | A1 * | 1/2009 | Virtanen et al. .............. 600/509 |

OTHER PUBLICATIONS

Gautama et al., A Differential Entropy Based Method for Determining the Optimal Embedding Parameters of a Signal, 2003, pp. 1-4.*

* cited by examiner

*Primary Examiner* — Jacqueline Cheng
*Assistant Examiner* — Puya Agahi
(74) *Attorney, Agent, or Firm* — Temmerman Law Office; Matthew J. Temmerman

(57) ABSTRACT

A method and system for sleep stage determination is disclosed comprising: acquiring EEG data from two or more EEG electrodes of an electrode arrangement, wherein the EEG data is divided into one or more epochs; detecting graphoelements from the EEG data for each epoch using a graphoelement detector; calculating a differential entropy from the EEG data for each epoch in an entropy module; and assigning a sleep stage to each epoch based on the calculated differential entropy and the detected graphoelements in a classifier module. This new method and system of sleep staging is potentially suited for, but not limited to, unattended sleep diagnostic scenarios.

7 Claims, 5 Drawing Sheets

METHOD AND SYSTEM FOR SLEEP STAGE DETERMINATION

FIELD

Generally, the described embodiments relate to methods and systems for sleep staging. In particular, the described embodiments involve a sleep stage determination system having a modified electrode setup using a reduced electrode set and an entropy-based method for sleep stage assignment that works with the modified electrode setup.

BACKGROUND

The diagnosis and treatment of many sleep-based disorders requires that the sleep of a patient be monitored using, for example, polysomnography (PSG). PSG is a comprehensive recording of the biophysiological changes that occur during sleep. PSG is a multi-parametric test that monitors many body functions, including brain, eye movements, muscle activity or skeletal muscle activation, heart rhythm, and breathing function or respiratory effort. Specifically, a patient's brain activity is monitored using electroencephalography (EEG), a measurement of electrical activity produced by the brain as recorded from electrodes placed on the scalp. Under current practice, at least four electrodes are placed near the central and occipital portions of the brain for obtaining EEG data. Additionally, a patient's eye movements are monitored using electrooculography (EOG), a measurement of electrical activity of the eyes as recorded from electrodes placed near both eyes. These electrodes provide a readout that can then be scored into different stages of sleep (e.g. wake, stage 1, stage 2, stage 3, stage 4, and rapid eye movement (REM)). A widely accepted method for scoring (i.e. assigning) different stages of sleep based on the presence of various graphoelements (e.g. SEM, BLINK, Spindle, K, Delta, Theta, and REM) is provided for in *A Manual of Standardized Terminology, Techniques, and Scoring System for Sleep Stages of Human Subjects*, edited by Allan Rechtschaffen and Anthony Kales (1968), commonly referred to as the R&K rules. The R&K rules prescribe an electrode setup consisting of four EEG channels and two EOG channels.

The complexity of many devices currently used in the field of sleep monitoring requires specialized training for their application and use. Currently, most sleep investigations must be performed in a laboratory environment. However, the diversity of sleep disorders and the specific nature of some of the treatments require recurrent investigations that are poorly suited for a laboratory environment due to both the cost and inconvenience to the patient. Moreover, monitoring the sleep of a patient in a laboratory environment may lead to error mainly because the patient has to sleep away from his or her bed during the investigation which affects the quality of sleep and potentially the diagnostic. While it would be desirable to migrate the sleep staging investigation from the specialized doctor's office to the home of the patient, attempts to implement unattended sleep staging have been hindered hitherto by the high failure rate of recordings due mainly to the patient's inappropriate application of electrodes because of lack of anatomical knowledge. Accordingly, there is a need for an improved method and system of sleep staging that is potentially suited for, but not limited to, unattended sleep diagnostic scenarios.

SUMMARY

A new method and system of sleep stage determination is presented below that is potentially suited for, but not limited to, unattended sleep diagnostic scenarios. The solution is twofold. First, it consists of a modified electrode setup or arrangement using a reduced electrode set that simplifies electrode application and therefore addresses the quality of the recording in unattended scenarios. Second, the solution is supported by an entropy-based method and system for sleep stage assignment that interpolates missing information due to the reduced spatial resolution of the modified electrode setup, but is not limited to use with this modified electrode setup.

In one aspect, there is provided a method for assigning sleep stages, the method comprising: acquiring EEG data from two or more EEG electrodes, wherein the EEG data is divided into one or more epochs; calculating a first entropy time-series and a second entropy time series from the EEG data for each epoch; calculating a differential entropy by taking the difference between the first entropy time-series and the second entropy time series; detecting a list of graphoelements from the EEG data for each epoch; and assigning a sleep stage for each epoch based on the calculated differential entropy and the detected graphoelements.

In another aspect, the step of assigning a sleep stage to each epoch comprises: if there are one or more detected graphoelements for each epoch and the calculated differential entropy of the epoch is contradictory to the one or more detected graphoelements, then the epoch is marked where the one or more detected graphoelements are predominantly detected as a particular sleep stage and not of any other sleep stage; and if there are no detected graphoelements for each epoch, then an epoch is assigned as a particular sleep stage by interpolating the calculated differential entropy of the epoch.

In another aspect, the method for assigning sleep stages further comprises: categorizing each epoch as light sleep or deep sleep based on the difference between the first entropy time-series and the second entropy time series for the epoch; if the specific epoch is categorized as light sleep, the differential entropy is minimum; and if the specific epoch is categorized as deep sleep, the differential entropy is maximum.

In another broad aspect, the method for assigning sleep stages further comprises: reclassifying a series of S1 epochs as REM epochs where any one of the S1 epochs in the series of S1 epochs has a variable entropy without increased EMG or increased SEM density.

In yet another aspect, there is provided a sleep staging system, the system comprising: an electrode arrangement comprising two or more EEG electrodes for acquiring EEG data, wherein the EEG data is divided into one or more epochs; an entropy module configured to calculate a differential entropy from the EEG data for each epoch; a graphoelement detector for detecting a list of graphoelements from the EEG data for each epoch; and a classifier module configured to assign a sleep stage for each epoch based on the calculated differential entropy and the detected graphoelements.

In another aspect, the classifier module is configured to assign a sleep stage for each epoch such that: if there are one or more detected graphoelements for each epoch, then an epoch is assigned with a particular sleep stage when the calculated differential entropy of the epoch is contradictory to the one or more detected graphoelements or assigned with a particular sleep stage when the calculated differential entropy of the epoch are not contradictory to the one or more detected graphoelements; and if there are no detected graphoelements in a specific epoch, then the epoch is assigned with a particular sleep stage by interpolating the calculated differential entropy of the epoch.

In another aspect, the classifier module is further configured to: categorize each epoch as light sleep or deep sleep based on the difference between the first entropy time series and the second entropy time-series for the specific epoch; if an epoch is categorized as light sleep, the differential entropy is minimum and an epoch is categorized as deep sleep the differential entropy is maximum.

In another aspect, the classifier module is further configured to: reclassify a series of S1 epochs as REM epochs where any one of the S1 epochs in the series of S1 epochs has a variable entropy without increased EMG or increased SEM density.

BRIEF DESCRIPTION OF THE DRAWINGS

A preferred embodiment of the present invention will now be described in detail with reference to the drawings, in which.

It will be appreciated that for simplicity and clarity of illustration, elements shown in the figures have not necessarily been drawn to scale. For example, the dimensions of some of the elements may be exaggerated relative to other elements for clarity.

DESCRIPTION OF EXEMPLARY EMBODIMENTS

It will be appreciated that for simplicity and clarity of illustration, where considered appropriate, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

Figure 1:
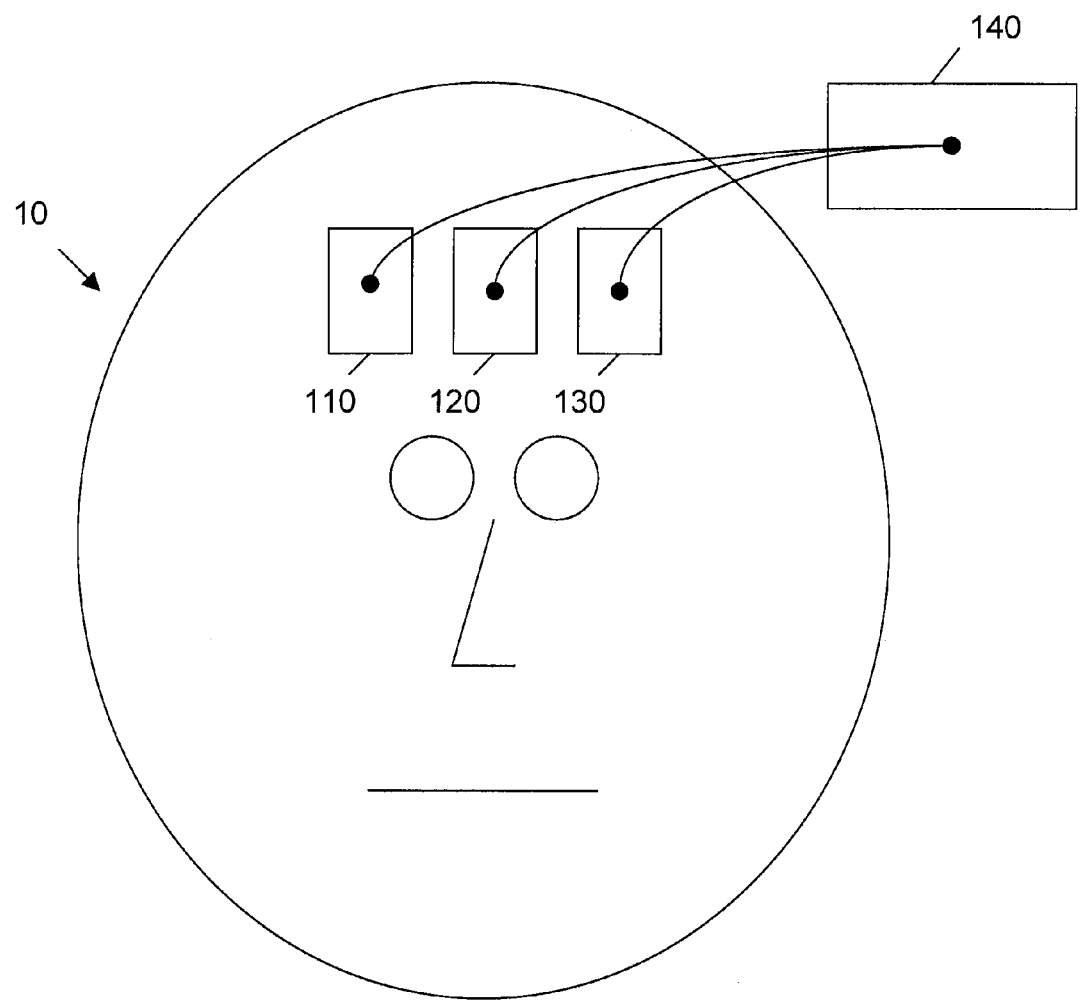
FIG. 1 is a diagram of an electrode arrangement according to various embodiments.

Reference is first made to FIG. 1 which depicts an electrode arrangement 10 according to some embodiments. As illustrated, electrode arrangement 10 comprises three EEG electrodes 110, 120 and 130 placed on the frontal area of a patient's head for measuring the electrical activity produced by the patient's brain which is collected as EEG data. In this embodiment, EEG electrodes 110, 120 and 130 are shown placed over the FP2, FPZ, and FP1 positions, respectively, in accordance with the International 10-20 System for EEG electrode placement. EEG electrodes 110 and 130 are active electrodes, while EEG electrode 120 (optional) serves as a Reference/Ground electrode. Although FIG. 1 illustrates a modified electrode setup using a reduced electrode set (i.e. electrode arrangement 10 having only two active EEG electrodes 110 and 130 and one Reference/Ground EEG electrode 120) for simplifying electrode application, in some other embodiments, additional active EEG electrodes and Reference/Ground EEG electrodes may be utilized.

In alternate embodiments (not shown), other known placements of EEG electrodes on the frontal area of a patient's head may be utilized. In further alternate embodiments (not shown), EEG electrodes may also be placed on any other easily accessible areas of a patient's head, including the temporal, central, parietal, and occipital regions.

Electrode arrangement 10 also comprises a data collection module 140. The data collection module 140 may be any recorder that can capture PSG data, for example, the TREX™ digital PSG system from XLTEK. Data collection module 140 may additionally amplify and digitize any captured PSG data for later processing. In the embodiment illustrated in FIG. 1, EEG data collected by electrodes 110, 120 and 130 are recorded and stored in data collection module 140. In other embodiments, data collection module 140 may also record and store additional signals (not shown) including, for example, additional EEG (e.g. C4-A1, C3-A2, O2-A1 and O1-A2), EOG, submental and bilateral tibial electromyogram (EMG), electrocardiogram (ECG), airflow (nasal-oral thermistor and nasal pressure, chest and abdominal movement (piezo bands), arterial oxyhemoglobin saturation, body position, and snoring intensity. These additional signals may be monitored using means known by persons skilled in the art. Furthermore, although FIG. 1 illustrates electrodes 110, 120 and 130 attached to data collection module 140 by an individual wire, in alternate embodiments (not shown), electrodes 110, 120 and 130 may be embedded into caps or nets.

By employing fewer electrodes than the current PSG practice prescribed by the widely accepted R&K rules of an electrode setup consisting of four EEG electrodes and two EOG electrodes, electrode arrangement 10 having a minimum two channels of EEG data simplifies the preparation and application of the electrodes which leads to improved quality of recording in unattended sleep diagnostic scenarios. Specifically, the modified electrode setup allows a patient to place the electrodes 110, 120 and 130 on his or her forehead easily without any assistance or anatomical knowledge. However, it should be noted that the reduced electrode set of electrode arrangement 10 renders the R&K rules for scoring different stages of sleep inapplicable. Accordingly, a new method and system of scoring different stages of sleep from a reduced electrode set is desirable. The new method and system should preferably be able to interpolate missing information due to the reduced spatial resolution of a modified electrode setup using a reduced electrode set, but should not be limited to use with this modified electrode setup.

Figure 2:
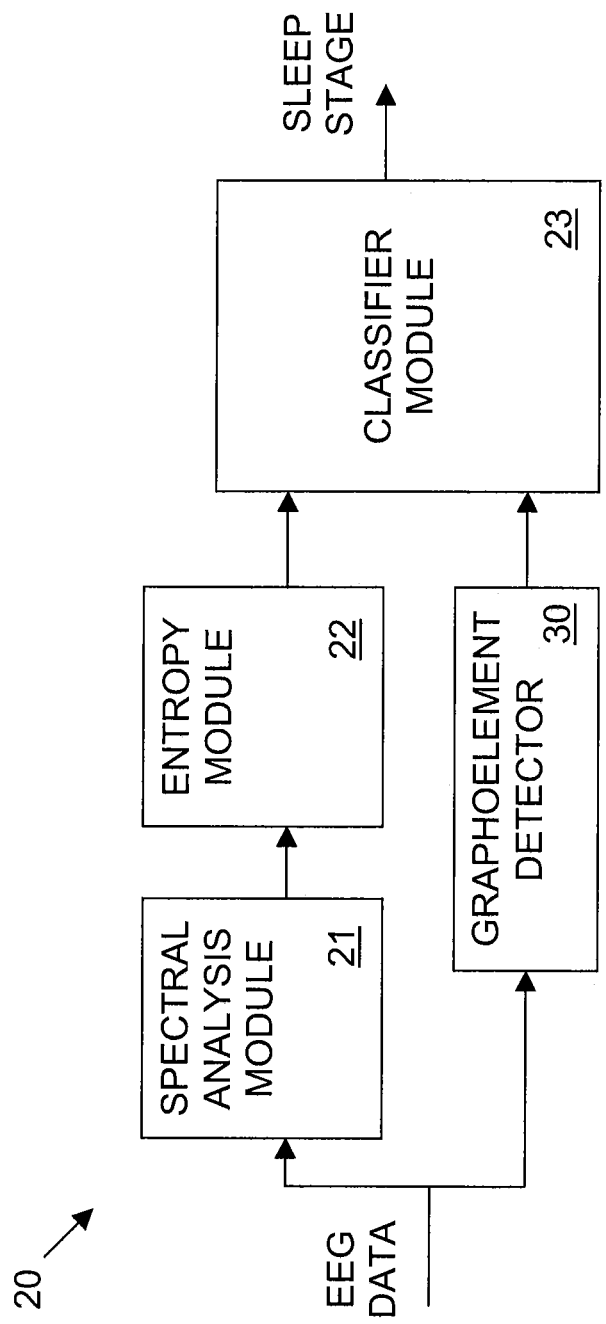
FIG. 2 is a block diagram of a sleep staging system for use with the electrode arrangement of FIG. 1.

Referring now to FIG. 2, a block diagram of a sleep staging system according to some embodiments is shown. Sleep staging system 20 comprises spectral analysis module 21, entropy module 22, graphoelement detector 30 and classifier module 23. Sleep staging system 20 receives EEG data as input and assigns a sleep stage as output. Specifically, sleep staging system 20 implements an entropy-based method and system for sleep stage assignment that interpolates missing information due to the reduced spatial resolution of the modified electrode setup described in FIG. 1, but is not limited to use with this modified electrode setup.

Sleep staging system 20 may be implemented in hardware or software, or a combination of both. For example, some embodiments may be implemented in computer programs operating on programmable computers each comprising at least one processor, a data storage system (including volatile and non-volatile memory and/or storage elements), at least one input device, and at least one output device. Other embodiments may be implement using programmable computer devices such as programmable logic arrays, programmable logic controllers, microcontrollers, microcomputers, personal computers, laptop computers, personal data assistants, and cellular telephones. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Sleep staging system 20 receives collected EEG data from data collection module 140 of FIG. 1. The EEG data may first be sampled, for example, at 200 Hz. The EEG data is provided to the spectral analysis module 21 and the graphoelement detector 30.

Spectral analysis module 21 performs spectral analysis of the EEG data. The EEG data is analyzed both in the time domain and the frequency domain in order to extract transients and rhythmic activity. Although time and frequency information are simply transformable into each other, the time domain is better suited for the recognition of transients while the frequency domain is better suited for the description of rhythmic activity. Spectral analysis may, for example, consist of a power spectral analysis in the standard EEG spectral bands. In addition, an EMG band can be considered above 45 Hz with the exclusion of a narrow band around the line frequency. The results of the spectral analysis module 21 are then provided to entropy module 22 for further processing.

Graphoelement detector 30 analyzes the EEG data to detect graphoelements. The implementation of graphoelement detector 30 will be described in greater detail below with reference to block diagram FIG. 3. The method of detecting graphoelements will be described in greater detail below with reference to flow chart FIG. 5 (specifically, method step 504). Graphoelement detector 30 provides a list of detected graphoelements to classifier module 23.

Entropy module 22 calculates the entropy of the EEG data, which represents the complexity of the neural tasks a patient's brain is engaged in at a particular moment in time. The method of calculating entropy will be described in greater detail below with reference to flow chart FIG. 5 (specifically, method step 502). Entropy module 22 provides the calculated entropy to classifier module 23.

Classifier module 23 uses the results from the graphoelement detector 30 and the entropy module 22 in a contextual manner to assign the appropriate sleep stage for the EEG data. Classifier module 23 classifies the EEG data by correlating the detected graphoelements with the calculated differential entropy. The method of classifying the EEG data as a particular sleep stage will be described in greater detail below with reference to flow chart FIG. 5 (specifically, method steps 506, 508, 510 and 512).

Figure 3:
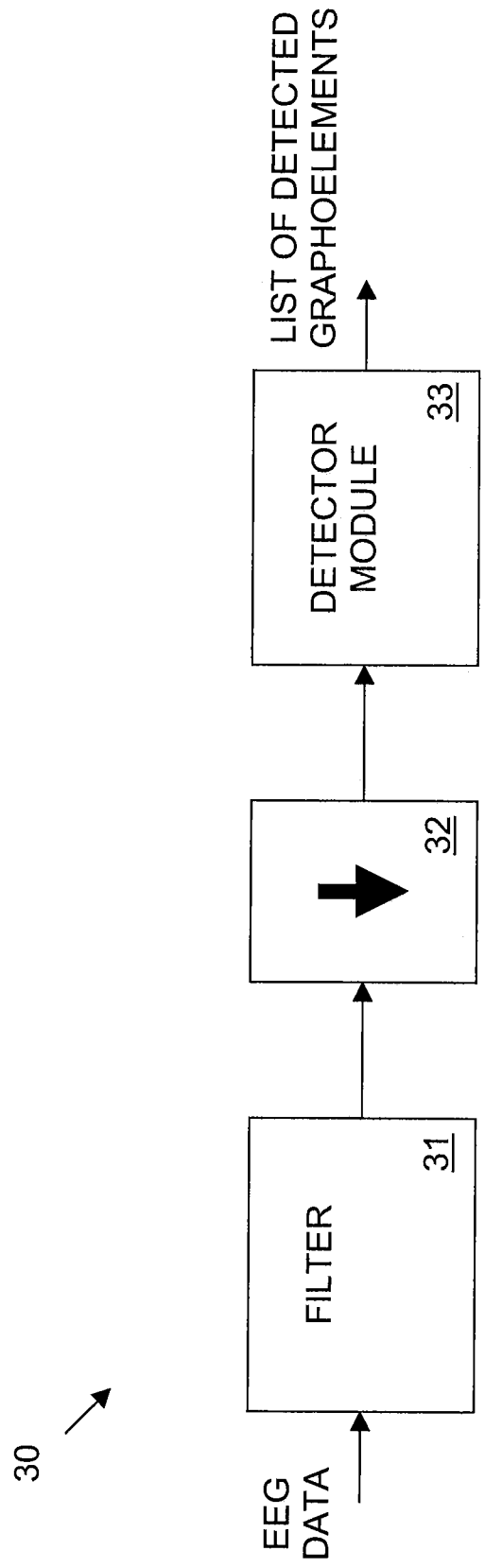
FIG. 3 is a block diagram of a graphoelement detector.

Referring now to FIG. 3, a block diagram of a graphoelement detector 30 of sleep staging system 20 (as illustrated in FIG. 2) is shown. Graphoelement detector 30 receives EEG data as input and produces a list of detected graphoelements as output. A multirate signal processing approach is adopted. Graphoelement detector 30 comprises a filter 31 (optional), a decimation module 32 (optional) and a detector module 33. It should be noted that filter 31 and decimation module 32 are optional as the EEG data signal may have already been filtered and decimated by means known to persons skilled in the art prior to being received by graphoelement detector 30 of sleep staging system 20.

Where filtering and decimation are required, filter 31 receives EEG data and filters it, for example, by characteristic band-pass filtering using a simple Butterworth filter, although any other filter known to those skilled in the art may be utilized. The filtered EEG data is then provided to decimation module 32. Decimation module 32 receives filtered EEG data from filter 31. Decimation module 32 decimates (or downsamples) the time-series of the filtered EEG data according to the spectral band of interest. For example, for a delta band 0.4-4 Hz, the EEG data can be decimated to 8 Hz. The decimated filtered EEG data is then provided to detector module 33.

Detector module 33 consists of a separate detector (not shown) for each type of graphoelement that can be monitored. Detector module 33 analyzes the EEG data to provide a list of detected graphoelements as output. For example, where electrodes are placed on the frontal area of a patient's head (e.g. as illustrated in FIG. 1), the following graphoelements are always visible on the frontal channels: delta activity, sleep spindles, EOG activity. Others graphoelements, like K complexes and alpha activity are only occasionally present or never present. The main operations of detector module 33 will be described in greater detail below with reference to flow chart FIG. 5 (specifically, method step 504).

Figure 4:
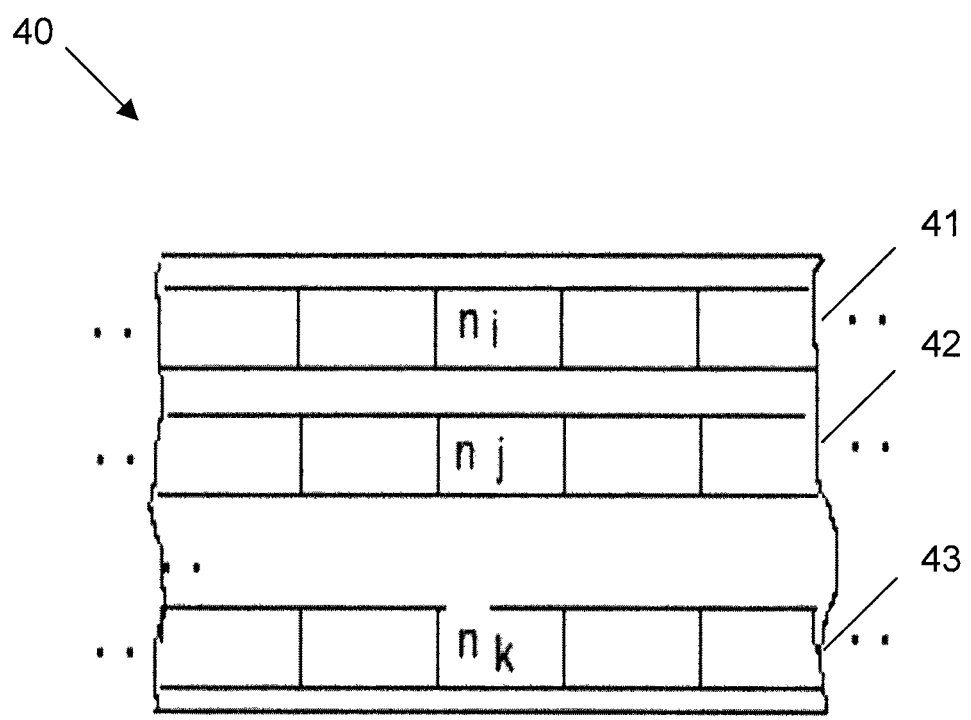
FIG. 4 is a diagram of a tape with sleep graphoelements.

Referring now to FIG. 4, a diagram of a tape 40 with sleep graphoelements is shown. Specifically, the list of detected graphoelements that is output by graphoelement detector 30 in FIG. 3 is presented on tape 40 where each separate detector of graphoelement detector 30 writes to a "track" 41, 42 and 43 on the tape 40 chronologically to indicate the detected features (i.e. those features that have contributed to the density of the corresponding operator) of each sleep graphoelement. The information presented on tape 40 represents amplitude and duration information and permits simplistic cross-correlation between detected features of each sleep graphoelement on ipsilateral channels. In this embodiment, $n_i$, $n_j$, $n_k$ indicate the density of graphoelements per unit time interval (i.e. the sleep epoch). Tape 40 may be a physical paper print-out or may be an imaged rendered digitally, for example, on a display monitor.

Figure 5:
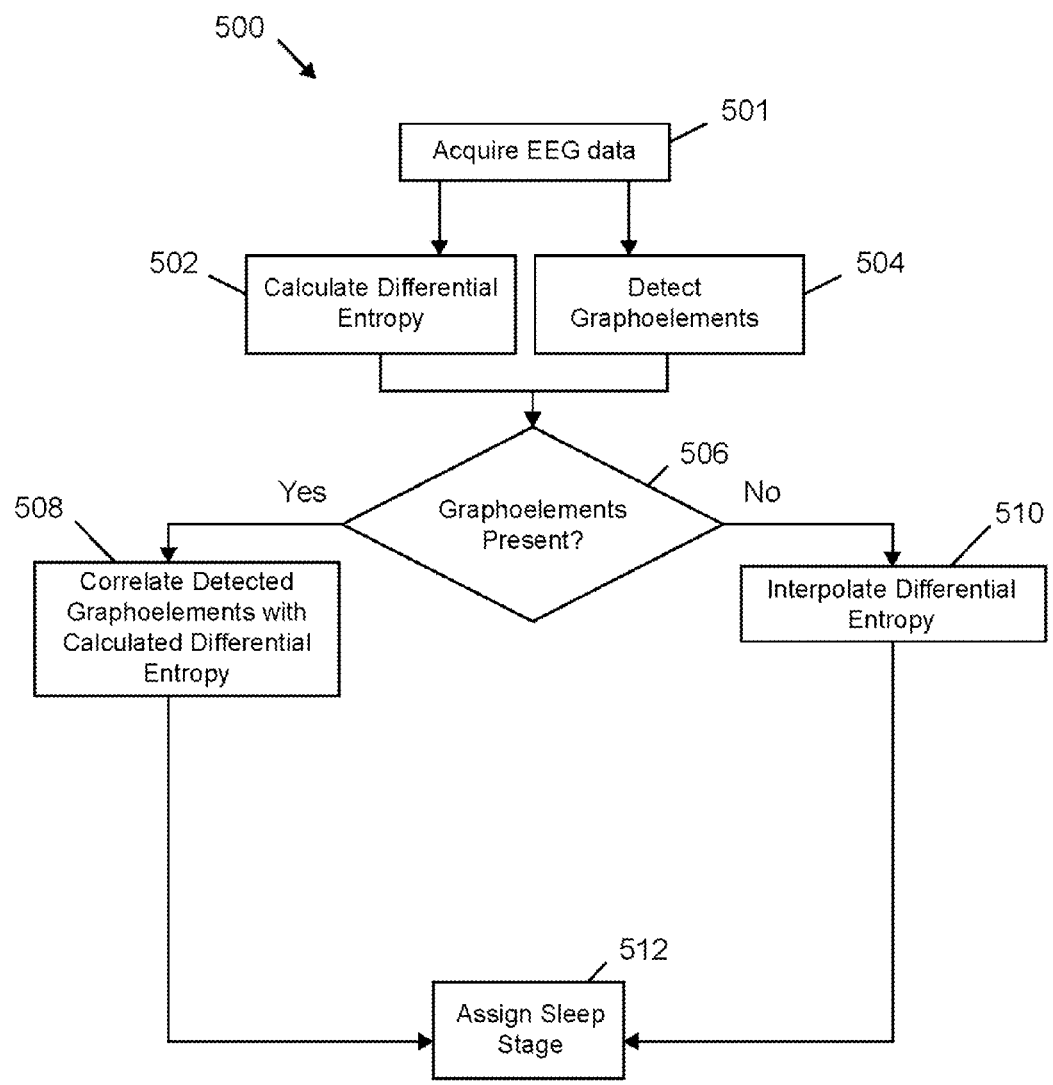
FIG. 5 is a flowchart of an example set of basic operational steps executed by the sleep staging system of FIG. 2.

Referring now to FIG. 5, a flowchart of an example method 500 executed by sleep staging system 20 of FIG. 2 according to some embodiments is shown. Method 500 processes acquired EEG data per unit time interval at step 501, or the sleep epoch, to assign a sleep stage of each epoch. For example, the sleep epoch may be set to 30 seconds, a time interval commonly used under current step staging practice.

The method 500 proceeds at steps 502 and 504 where entropy is calculated and graphoelements are detected using acquired EEG data.

At step 502, performed by entropy module 22 of sleep staging system 20, the entropy of the EEG data, which represents the complexity of the neural tasks a patient's brain is engaged in at a particular moment in time, is calculated. Specifically, entropy module 22 calculates the entropy of the time-series.

A central element in statistical mechanics is the concept of entropy. Entropy is proportional to the number of states compatible with a given macroscopic state. In other words, $S \alpha \ln \Omega$ where S is the entropy and $\Omega$ is the number of states compatible with the macroscopic state. The logarithm transforms the probability of independent states which is multiplicative to an additive measure compatible with the extensive nature of the entropy. In the brain, macroscopic states are basically states of consciousness and sensations, while microscopic states are represented by the momentary states of neurons. There are large numbers of microstates compatible with particular macroscopic states.

The number of compatible states can be estimated in a number of ways. In this embodiment, the spectral mapping of the time-series using the Fourier transform is used. In alternate embodiments, the data may be used directly but some detrending and additional processing would have to be performed to eliminate interfering states or any other mapping.

First, the probability density of the power spectrum of the EEG data is estimated. The power spectrum of a stochastic signal is the Fourier transform of the autocorrelation function. The probability is inversely proportional to the number of accessible states (e.g. the unequivocal state, the state with probability one of occurrence will give a state of zero entropy). Average properties of macroscopic systems can be estimated only after estimating the probabilities of various microscopic states. Let $EEG_i$ represent the spectrum of the second order:

$$EEG_i(\omega) \overset{F}{\leftrightarrow} \int c_2^{ij}(t)e^{-j\omega t}\,dt$$

$$c_2^{ij}(\tau) = E\{eeg_i(t) \cdot eeg_j^*(t+\tau)\}$$

By using a standard estimation of the probability density of the spectral data, the following histogram is completed:

$$H(n) = \left\{ \begin{array}{l} \text{card}(t_n < EEG_i(k) < t_{n+1} | k \in (0, N), n < M, \\ t_n = n * \dfrac{\max(EEG_i(k)) - \min(EEG_i(k))}{M} \end{array} \right\}$$

Therefore, the entropy of the time-series is defined as follows:

$$H(EEG_i(k)) = -\frac{1}{N}\sum H[n] \ln \frac{H[n]}{N}$$

The entropy is a quantifier of the complexity of the neural tasks the brain is engaged in at a moment in time.

Additional constraints may be imposed based on heuristics. For instance, the trajectories from specified volumes in phase space can be excluded by creating infinite potential walls between phase space domains. This can be accomplished by excluding specific frequency bands that are specific to some states only. Such a methodology can be used to implement a differential method that handles differently various planes of sleep by creating groupings thereof.

In this embodiment, two entropy time-series with a resolution of one second each are obtained. One entropy time-series characterizes states of light sleep and the other characterizes all states including light sleep. The entropy obtained from the constrained data set is denoted $H_1(EEG_i(k))$ and the entropy computed from the full data set is denoted $H(EEG_i(k))$. The differential entropy of the two time-series characterizes deep sleep and light sleep and is denoted $H_D(EEG_i(k)) = H(EEG_i(k)) - H_1(EEG_i(k))$. The absolute value of differential entropy will be maximal during states of deep sleep and minimal during states of light sleep. All entropy series may be smoothed using median filtering of order 10 for easier interpretation of the time-series and alignment with the sleep epoch (e.g. 30 second boundaries).

In some embodiments, the calculated entropy may be utilized for calibration purposes. The level of entropy for the wake state may be calibrated at the point where the variance of the EMG power time-series falls below a threshold and the entropy has fallen below stage 1 entropy. This step is recommended only to eliminate small inter-patient variability and the variable noise conditions of different recordings. The level of entropy corresponding to the point where the EMG power increased by a preset factor may be marked as the entropy of the wake state. All thresholds for individual stages may then be adjusted to this reference evenly.

At step 504, performed by graphoelement detector 30 of sleep staging system 20, graphoelements present in the EEG data are detected. Specifically, the EEG data is analyzed to detect graphoelements.

The input to detector module 33 of graphoelement detector 30 can be denoted as $eeg_i[n]$, where $i \in \{1,2\}$. The signal can then be derivated to obtain:

$$deegi[n] = \frac{deeg_i}{dt}$$

The following set can then be built:

$$Zx = \left\{ \begin{array}{l} n | deeg_i[n] \cdot deeg_i[n+1] <= 0 \wedge \\ |eeg[n] - eeg[Zz[\text{card}Zx - 1]]| > thr \wedge \\ deeg_i[n+m] \cdot deeg_i[n+m+1] <= 0 \wedge \\ |eeg[n+m] - eeg[n]| > thr, m > 0 \end{array} \right\}$$

The set Zx contains candidate wavelet boundaries. Each separate detector of detector module 33 contains a template against which the wavelet is compared. This template consists of min-max amplitude and duration thresholds. For some detectors, if a template match is found, the max probability of the data is estimated by estimating the probability distribution of the wavelet data. Specifically, $$p_{max} = \max(H(a))$$

where H(a) is the Histogram as a function of bin characteristic value a. For example, a number of 10 bins may be satisfactory for this purpose.

For the delta detector the following ratio is computed:

$$r = \frac{eeg[Zz[cardZx - 2]] - b}{eeg[Zz[cardZx - 3]] - b}$$

where $b=H^{-1}(p_{max})$ represents the characteristic value of the most probable value of the previous second to the wavelet under scrutiny. The value r is tested against a prescribed threshold in order to eliminate slow wavelets that are not of cerebral origin.

The density of graphoelements per epoch can be computed using the following equation:

$$n_i = \sum_{j}^{cardZx} T(Zx\{j-1, j, j+1\}, eeg)b(r_j, p_j, c_{12}),$$

where j is scanned over all wavelets in an epoch. In the above equation, i represents the graphoelement, T represents the template operator applied to the set Zx and data set eeg, and b(r,p) is a Boolean function. For most of the detectors b(r,p)=1. However, for the delta detector, b(r,p)= $(t_1<r<t_2 \| p<0.3)$; for the BLINK detector, b(r,p)=$c_{12}>0.7$; for the SEM detector, b(r,p)=$c_{12}<-0.7$; and for the REM detector, b(r,p)=$c_{12}<-0.7$. The correlation coefficient is represented by $c_{12}$:

$$c_{12} = \frac{n\sum_{Zx(n-1)}^{Zx(n+1)} x_i y_i - \sum_{Zx(n-1)}^{Zx(n+1)} x_i \sum_{Zx(n-1)}^{Zx(n+1)} y_i}{\sqrt{n\sum_{Zx(n-1)}^{Zx(n+1)} x_i^2 - \left(\sum_{Zx(n-1)}^{Zx(n+1)} x_i\right)^2} \sqrt{n\sum_{Zx(n-1)}^{Zx(n+1)} y_i^2 - \left(\sum_{Zx(n-1)}^{Zx(n+1)} y_i\right)^2}}$$

and $x=eeg_1$ $y=eeg_2$.

At step 506, once graphoelements have been detected and entropy calculated from the EEG data for a particular epoch, it is determined whether grapholements are present in that epoch.

If graphoelements are found at step 506, then the detected graphoelements are correlated with the calculated differential entropy at step 508. Specifically, at step 508, it is determined whether the sleep stage corresponding to the detected graphoelements (in accordance with the following table) matches the sleep stage as determined by the calculated differential entropy:

TABLE 1

| Graphoelement | Sleep stage (Sx) |
|---|---|
| SEM | S1 |
| BLINK | W |
| Spindle | S2 |
| K | S2 |
| Delta | S3, S4 |
| Theta | S1 |
| REM | REM, W |

If the sleep stage as determined by the detected graphoelements and the calculated entropy are not contradictory, then a particular sleep stage is assigned at step 512 by marking the epoch where the graphoelements were detected as the sleep stage corresponding to the entropy level. However, if the detected graphoelements and the calculated differential entropy are contradictory, then a particular sleep stage is assigned at step 512 in accordance with the dominant of the contradictory detected graphoelements; i.e., the epoch is marked such that where the graphoelements are predominantly detected contradictory to the differential entropy as the particular sleep stage and not of any other sleep stage. If the graphoelement is considered contradictory to the differential entropy, the particular sleep stage is assigned, and the graphoelement does not correspond to the differential entropy according to Table 1 (above).

The determination of the sleep stage can be condensed in the following formal relation:

$$Sx = H(x) \cdot G(x)$$

$$G(x) = \begin{cases} 1 & \text{if } n_i \in Sx, n_i > n_j n_i > t \forall i \neq j \\ 0 & \end{cases}$$

The above relation can be translated: a stage X is detected when the entropy of the epoch is H(x) corresponding to that stage X, the graphoelements during the epoch are predominantly of stage X and not of any other stage.

If no graphoelements are found at step 506 (i.e., no graphoelements are detected), then the differential entropy is interpolated based on the first entropy time-series and the second entropy time-series at step 510.

For the interpolated sections, at step 510, it is determined if the sleep is light or deep based on the differential entropy. For example, if the algorithm detects sleep spindles and light sleep by low differential entropy, then the sleep stage is classified as light sleep. As a further example, if there is a significant density of delta validated by high differential entropy, then the sleep stage is classified as deep sleep.

If deep sleep is detected, then the differential entropy will be used to refine the stage at step 510 so that a particular sleep stage may be assigned at step 512. Specifically, the differential entropy is maximal in deep sleep and insignificant in light sleep.

As part of the assignment undertaken at step 512, an optional step may be performed in order to avoid misclassification of transient epochs during REM (not shown). Specifically, if stage S1 is determined, the stage is retained until the whole chain that includes this epoch ends, namely until some other stage is found and the new sleep state is persistent (i.e., it is not switching back to S1 for a number of prescribed epochs). A chain is defined as a set of staged epochs with the same designation.

As part of the assignment undertaken at step 512, REM sleep is classified. One of the new problems introduced with the modified electrode setup presented in FIG. 1 is the lack of consistency in EOG signal polarity due to the new positioning of the electrodes. In order to avoid significant REM classification errors, REM may be detected based on the calculated entropy. Specifically, the median entropy during REM corresponds to S1 and local variability is disturbed by occasional REMs. The REM stage may be assigned by the detection of light sleep with no graphoelements like spindles and K, entropy corresponding to S1 and specific variation of the entropy corresponding to REMs. The lack of variation of entropy will preserve the state of the chain, which in this case will be S1. An increased level of EMG activity will invalidate REM staging and preserve the state of the chain as well. If, during an S1 chain, potential REM activity is determined and there is no conflicting information like increased EMG or increased SEM density, all S1 detections in the chain containing the REM activity will be reclassified as REM.

Accordingly, a new method and system of sleep stage determination that is potentially suited for, but not limited to, unattended sleep diagnostic scenarios has been presented above. The solution is twofold. First, it consists of a modified electrode setup using a reduced electrode set that simplifies electrode application and therefore addresses the quality of the recording in unattended scenarios. Second, the solution is supported by an entropy-based method and system for sleep stage assignment that interpolates missing information due to the reduced spatial resolution of the modified electrode setup, but is not limited to use with this modified electrode setup. The results obtained with this new method and system of sleep stage determination are comparable to that determined by a human scorer using conventional R&K rules for sleep scoring. Use of this new method and system of sleep stage determination presented above can bridge the technological gap that was in the way of expanding the sleep lab into the patient's home and, therefore, meets one of the most important future challenges for sleep medicine, its cost-effective expansion.

The present invention has been described here by way of example only. Various modification and variations may be made to these exemplary embodiments without departing from the spirit and scope of the invention, which is limited only by the appended claims.

The invention claimed is:

1. A method for assigning sleep stages using a reduced electrode setup wherein the patient is in an unattended sleep diagnostic scenario, the method comprising:
    acquiring electroencephalograph (EEG) data from two or more EEG electrodes of an electrode arrangement that is adapted to be attached on a frontal area of a patient's head;
    processing, at a processor, the EEG data into one or more epochs;
    recording, at the processor, the EEG data;
    analyzing, at the processor, the EEG data both in time domain and frequency domain so as to extract transients and rhythmic activity;
    calculating, at the processor, a first entropy time-series and a second entropy time-series from the EEG data for each said epoch, wherein the first entropy time-series characterizes states of light sleep and the second entropy time-series characterizes all sleep states including light sleep;
    calculating, at the processor, a differential entropy by subtracting the first entropy time-series from the second entropy time-series;
    assigning, at the processor, an epoch as light sleep when the absolute value of the differential entropy is minimum or deep sleep when the absolute value of the differential entropy is maximum;
    detecting, at the processor whether at least one graphoelement is present from the EEG data for each epoch;
    interpolating, at the processor, the differential entropy if there are no detected graphoelements, and if there are one or more detected graphoelements, then correlating the at least one graphoelement with the differential entropy; and
    assigning a particular sleep stage for the epoch when the one or more detected graphoelements and differential entropy are not contradictory to each other or assigning a particular sleep stage and not of any other sleep stage for the epoch when the one or more detected graphoelements and differential entropy are contradictory to each other.

2. The method of claim 1, the method further comprising:
    reclassifying a series of S1 epochs as rapid eye movement (REM) epochs where any one of the S1 epochs in the series of S1 epochs has a variable entropy without increased electromyogram (EMG) or increased slow eye movement (SEM) density.

3. A sleep staging system using a reduced electrode setup wherein the patient is in an unattended sleep diagnostic scenario, the system comprising:
    an electrode arrangement comprising two or more EEG electrodes such that at least one of the electrodes is a reference EEG electrode and at least a second of the electrodes is an active EEG electrode and wherein the electrode arrangement is adapted to be attached on a frontal area of a patient's head to measure brain electrical activity of the patient for acquiring EEG data;
    a processor in electronic communication with the electrode arrangement, the processor being configured to process the EEG data into one or more epochs, the processor comprising:
        a data collection module electrically connected to the electrode arrangement and being configured to receive, record and store the EEG data from the two or more EEG electrodes;
        a spectral analysis module electrically connected to the data collection module and being configured to receive and analyze the EEG data both in time domain and frequency domain so as to extract transients and rhythmic activity;
        an entropy module electrically connected to the spectral analysis module and being configured to:
            calculate a first entropy time-series and a second entropy time-series of the EEG data for each epoch, wherein the first entropy time-series characterizes states of light sleep and the second entropy time-series characterizes all sleep states including light sleep; and
            calculate a differential entropy by subtracting the first entropy time-series from the second entropy time-series;
        a graphoelement detector electrically connected to the data collection module being configured for detecting whether one or more graphoelements is present from the EEG data for each epoch; and
        a classifier module electrically connected to the entropy module and the graphoelement detector being configured to assign a sleep stage for each epoch based on the differential entropy and whether one or more graphoelements is present.

4. The sleep staging system of claim 3, wherein the classifier module is configured to assign a sleep stage for each epoch based on the differential entropy and whether one or more graphoelements is present such that:
    if there is one or more graphoelements present for each epoch, then the detected one or more graphoelements is correlated with the differential entropy, then if the detected one or more graphoelements and differential entropy are not contradictory to each other, then the epoch where the graphoelements were detected corresponding to the differential entropy is assigned as a particular sleep stage or if the detected one or more graphoelements and the differential entropy are contradictory to each other, then the epoch where the one or more detected graphoelements were predominantly detected contradicting to the differential entropy is assigned as a particular sleep stage and not of any other sleep stage; and if there are no detected graphoelements for each epoch, then the differential entropy of the first entropy time-series and the second entropy time-series are interpolated such that when the differential entropy is maximum the epoch is assigned as deep sleep and when the differential entropy is minimum the epoch is assigned as light sleep.

5. The sleep staging system of claim 3, wherein the classifier module is further configured to:
reclassify a series of S1 epochs as REM epochs where any one of the S1 epochs in the series of S1 epochs has a variable entropy without increased EMG or increased SEM density.

6. The sleep staging system of claim 3, wherein the graphoelement detector further comprises:
a filter configured to receive and filter the EEG data;
a decimation module configured to decimate time-series of the filtered EEG data; and
a detector module configured to analyze the decimated filtered EEG data to provide a list of detected graphoelements as output, the detector module includes a separate detector to monitor each type of graphoelement.

7. The method of claim 1, wherein the step of detecting step further comprises:
receiving the EEG data and filtering the EEG data using a filter;
decimating time-series of the filtered EEG data using a decimation module; and
receiving the decimated filtered EEG data and analyzing the decimated filtered EEG data to provide a list of graphoelements as output using a detector module.

* * * * *